(12) United States Patent
Demetriades et al.

(10) Patent No.: US 8,202,311 B2
(45) Date of Patent: Jun. 19, 2012

(54) STENT/GRAFT DEVICE AND METHOD FOR OPEN SURGICAL PLACEMENT

(75) Inventors: Demetrios Demetriades, Los Angeles, CA (US); Bruce Gingles, Bloomington, IN (US); James B. Hunt, Bloomington, IN (US); Charles L. McIntosh, Silver Spring, MD (US)

(73) Assignee: Cook Medical Technologies LLC, Bloomington, IN (US)

( * ) Notice: Subject to any disclaimer, the term of this patent is extended or adjusted under 35 U.S.C. 154(b) by 581 days.

(21) Appl. No.: 11/493,076

(22) Filed: Jul. 26, 2006

(65) Prior Publication Data
US 2007/0027526 A1    Feb. 1, 2007

Related U.S. Application Data

(60) Provisional application No. 60/702,924, filed on Jul. 27, 2005.

(51) Int. Cl.
*A61F 2/06* (2006.01)

(52) U.S. Cl. ...................... 623/1.13; 623/903

(58) Field of Classification Search .............. 128/898; 606/108, 152–155, 8; 623/1.11–1.16, 1.23, 623/1.36, 903
See application file for complete search history.

(56) References Cited

U.S. PATENT DOCUMENTS

| | | | |
|---|---|---|---|
| 3,657,744 A | 4/1972 | Ersek | 3/1 |
| 4,313,231 A | 2/1982 | Koyamada | 3/1.4 |
| 4,580,568 A | 4/1986 | Gianturco | 128/345 |
| 4,728,328 A | 3/1988 | Hughes et al. | 623/12 |
| 4,787,899 A | 11/1988 | Lazarus | 623/1 |
| 5,078,726 A | 1/1992 | Kreamer | 606/194 |
| 5,104,399 A * | 4/1992 | Lazarus | 623/1.14 |
| 5,152,782 A | 10/1992 | Kowligi et al. | 623/1 |
| 5,275,622 A | 1/1994 | Lazarus et al. | 623/1 |
| 5,282,824 A | 2/1994 | Gianturco | 606/108 |
| 5,316,023 A | 5/1994 | Palmaz et al. | 128/898 |
| 5,330,490 A | 7/1994 | Wilk et al. | 606/153 |
| 5,360,443 A | 11/1994 | Barone et al. | 623/1 |
| 5,425,765 A | 6/1995 | Tiefenbrun et al. | 623/12 |
| 5,456,712 A | 10/1995 | Maginot | 623/1 |
| 5,476,506 A | 12/1995 | Lunn | 623/1 |
| 5,489,295 A | 2/1996 | Piplani et al. | 623/1 |
| 5,522,880 A | 6/1996 | Barone et al. | 623/1 |
| 5,522,881 A | 6/1996 | Lentz | 623/1 |
| 5,522,883 A | 6/1996 | Slater et al. | 623/1 |
| 5,527,355 A | 6/1996 | Ahn | 623/1 |
| 5,562,728 A | 10/1996 | Lazarus et al. | 623/1 |
| 5,575,817 A | 11/1996 | Martin | 623/1 |

(Continued)

FOREIGN PATENT DOCUMENTS
DE    101 04 806 A1    8/2002
(Continued)

*Primary Examiner* — Ryan Severson
*Assistant Examiner* — Ashley Cronin
(74) *Attorney, Agent, or Firm* — Brinks Hofer Gilson & Lione

(57) ABSTRACT

A method and a stent/graft device for intraoperative repair of a damaged portion of a body vessel. The stent/graft device has a length at least as long as the length of the damaged portion of the vessel undergoing repair, and is positioned within the vessel such that the device at least spans the length of the damaged vessel portion. The stent/graft device is securely engaged with the vessel at the site of the damage in a manner such that migration of the device in said vessel is inhibited.

22 Claims, 5 Drawing Sheets

U.S. PATENT DOCUMENTS

| | | | |
|---|---|---|---|
| 5,578,071 A | 11/1996 | Parodi | 623/1 |
| 5,578,072 A | 11/1996 | Barone et al. | 623/1 |
| 5,591,195 A | 1/1997 | Taheri et al. | 606/194 |
| 5,591,229 A | 1/1997 | Parodi | 623/1 |
| 5,628,783 A | 5/1997 | Quiachon et al. | 623/1 |
| 5,653,736 A * | 8/1997 | Glastra | 606/198 |
| 5,720,776 A | 2/1998 | Chuter et al. | 623/1 |
| 5,755,770 A | 5/1998 | Ravenscroft | 623/1 |
| 5,769,882 A | 6/1998 | Fogarty et al. | 623/1 |
| 5,824,040 A | 10/1998 | Cox et al. | 623/1 |
| 5,824,041 A | 10/1998 | Lenker et al. | 623/1 |
| 5,843,173 A | 12/1998 | Shannon et al. | 623/1 |
| 5,928,279 A | 7/1999 | Shannon et al. | 623/1 |
| 6,048,360 A * | 4/2000 | Khosravi et al. | 623/1.11 |
| 6,139,572 A | 10/2000 | Campbell et al. | 623/1.11 |
| 6,162,246 A | 12/2000 | Barone | 623/1.35 |
| 6,267,783 B1 | 7/2001 | Letendre et al. | 623/1.13 |
| 6,306,164 B1 | 10/2001 | Kujawski | 623/1.35 |
| 6,315,792 B1 * | 11/2001 | Armstrong et al. | 623/1.23 |
| 6,319,278 B1 | 11/2001 | Quinn | 623/1.13 |
| 6,352,553 B1 | 3/2002 | van der Burg et al. | 623/1.23 |
| 6,352,561 B1 | 3/2002 | Leopold et al. | 623/1.23 |
| 6,409,756 B1 | 6/2002 | Murphy | 623/1.35 |
| 6,432,131 B1 | 8/2002 | Ravenscroft | 623/1.13 |
| 6,451,047 B2 * | 9/2002 | McCrea et al. | 623/1.13 |
| 6,451,051 B2 | 9/2002 | Drasler et al. | 623/1.15 |
| 6,517,570 B1 | 2/2003 | Lau et al. | 623/1.13 |
| 6,547,815 B2 | 4/2003 | Myers | 623/1.13 |
| 6,613,072 B2 | 9/2003 | Lau et al. | 623/1.11 |
| 6,663,667 B2 | 12/2003 | Dehdashtian et al. | 623/1.51 |
| 6,767,359 B2 | 7/2004 | Weadock | 623/1.13 |
| 6,770,087 B2 * | 8/2004 | Layne et al. | 623/1.13 |
| 6,780,497 B1 | 8/2004 | Walter | 428/311.51 |
| 6,814,748 B1 | 11/2004 | Baker et al. | 623/1.14 |
| 6,852,122 B2 | 2/2005 | Rush | 623/1.13 |
| 6,878,164 B2 | 4/2005 | Kujawski et al. | 623/1.36 |
| 6,911,042 B2 | 6/2005 | Weadock | 623/1.23 |
| 6,949,119 B2 | 9/2005 | Myers | 623/1.13 |
| 7,022,133 B2 | 4/2006 | Yee et al. | 623/1.11 |
| 7,044,961 B2 | 5/2006 | Lentz et al. | 623/1.13 |
| 7,083,631 B2 | 8/2006 | Houser et al. | 606/153 |
| 7,122,052 B2 | 10/2006 | Greenhalgh | 623/1.35 |
| 7,691,135 B2 | 4/2010 | Shaolian et al. | 623/1.11 |
| 7,736,388 B2 | 6/2010 | Goldfarb et al. | 623/2.11 |
| 7,780,720 B2 | 8/2010 | Goicoechea et al. | 623/1.16 |
| 7,794,487 B2 | 9/2010 | Majercak et al. | 623/1.11 |
| 2002/0091439 A1 | 7/2002 | Baker et al. | 623/1.36 |
| 2002/0107535 A1 | 8/2002 | Wei et al. | 606/155 |
| 2003/0074055 A1 | 4/2003 | Haverkost | 623/1.16 |
| 2003/0120331 A1 | 6/2003 | Chobotov et al. | 623/1.13 |
| 2003/0158595 A1 | 8/2003 | Randall et al. | 623/1.13 |
| 2004/0044358 A1 | 3/2004 | Khosravi et al. | 606/194 |
| 2004/0098092 A1 | 5/2004 | Butaric et al. | 623/1.13 |
| 2004/0098096 A1 | 5/2004 | Eton | 623/1.13 |
| 2004/0106978 A1 | 6/2004 | Greenberg et al. | 623/1.13 |
| 2004/0193245 A1 | 9/2004 | Deem et al. | 623/1.13 |
| 2004/0199241 A1 | 10/2004 | Gravett et al. | 623/1.13 |
| 2004/0204753 A1 | 10/2004 | Shokoohi et al. | 623/1.16 |
| 2004/0215338 A1 * | 10/2004 | Elkins et al. | 623/1.46 |
| 2005/0021126 A1 | 1/2005 | Machan et al. | 623/1.13 |
| 2005/0033400 A1 | 2/2005 | Chuter | 623/1.11 |
| 2005/0038502 A1 | 2/2005 | Waysbeyn et al. | 623/1.23 |
| 2005/0049672 A1 | 3/2005 | Murphy | 623/1.12 |
| 2005/0049674 A1 | 3/2005 | Berra et al. | 623/1.13 |
| 2005/0070992 A1 | 3/2005 | Bolduc et al. | 623/1.15 |
| 2005/0080482 A1 | 4/2005 | Bonsignore | 623/1.35 |
| 2005/0090843 A1 | 4/2005 | Bolduc | 606/151 |
| 2005/0096737 A1 | 5/2005 | Shannon et al. | 623/1.44 |
| 2005/0154443 A1 | 7/2005 | Linder et al. | 623/1.11 |
| 2005/0154448 A1 | 7/2005 | Cully et al. | 623/1.15 |
| 2005/0171594 A1 | 8/2005 | Machan et al. | 623/1.13 |
| 2005/0187604 A1 | 8/2005 | Eells et al. | 623/1.13 |
| 2005/0240258 A1 | 10/2005 | Bolduc et al. | 623/1.27 |
| 2005/0240260 A1 | 10/2005 | Bolduc | 623/1.36 |
| 2005/0266042 A1 | 12/2005 | Tseng | 424/423 |
| 2005/0273155 A1 | 12/2005 | Bahler et al. | 623/1.13 |
| 2005/0288767 A1 | 12/2005 | Kujawski et al. | 623/1.13 |
| 2006/0064156 A1 * | 3/2006 | Thistle et al. | 623/1.16 |
| 2006/0259125 A1 * | 11/2006 | Peacock, III | 623/1.12 |

FOREIGN PATENT DOCUMENTS

| | | |
|---|---|---|
| FR | 2 768 921 A1 | 10/1997 |
| JP | 06-319755 A | 11/1994 |
| WO | WO 96/39999 | 12/1996 |
| WO | WO 96/39999 A1 | 12/1996 |
| WO | WO 02/15823 A2 | 2/2002 |
| WO | WO 03/082152 A1 | 10/2003 |

* cited by examiner

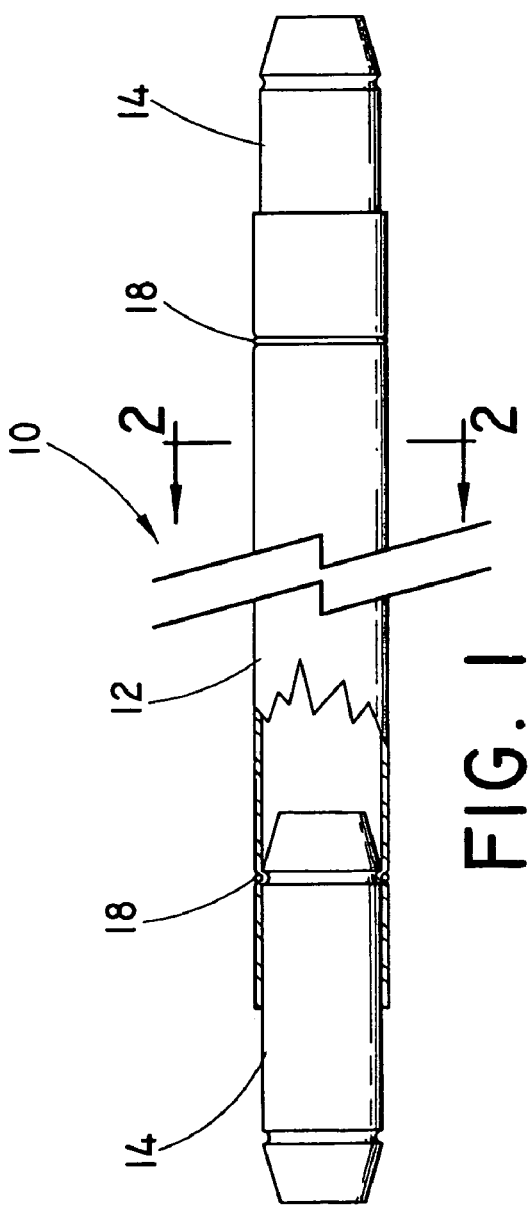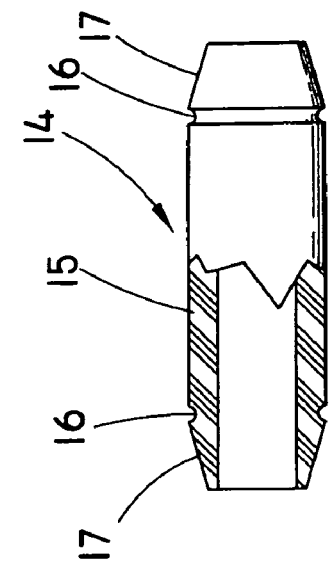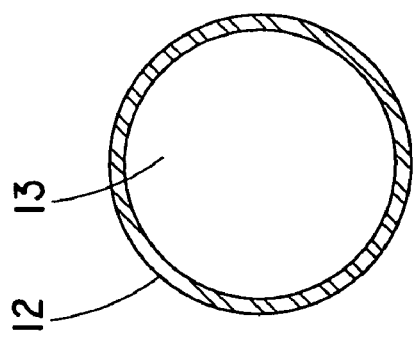

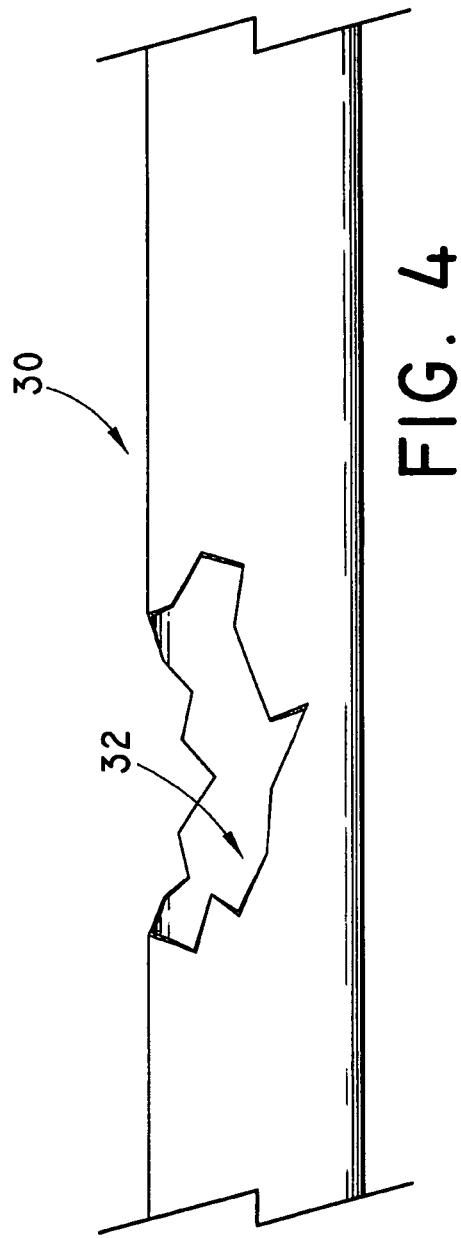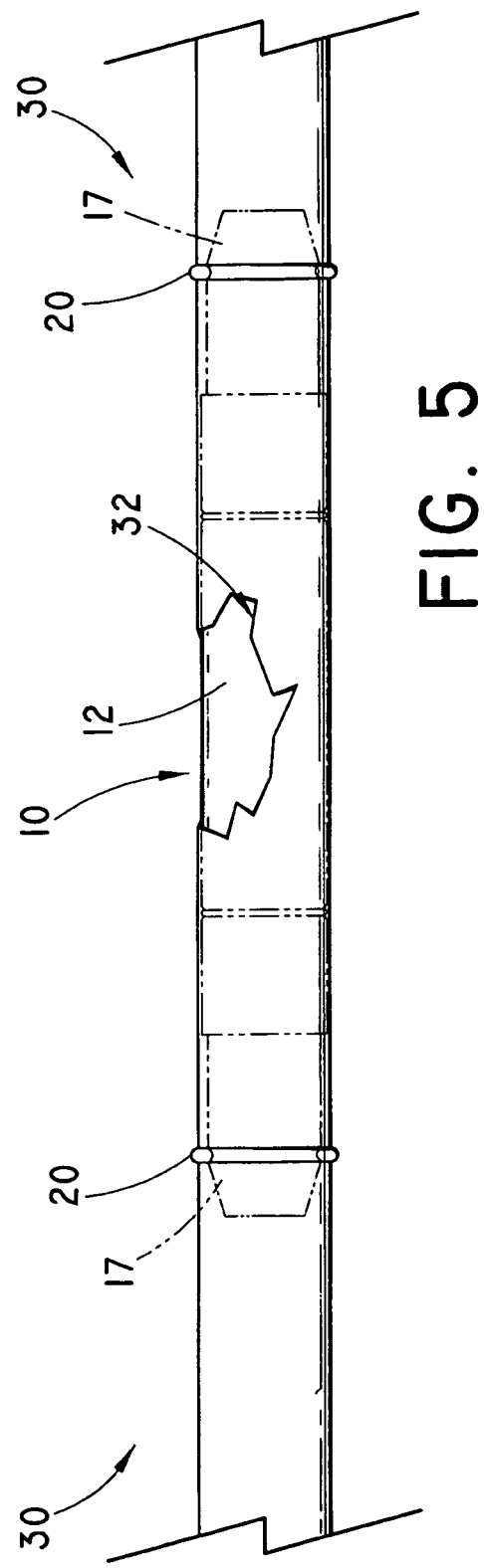

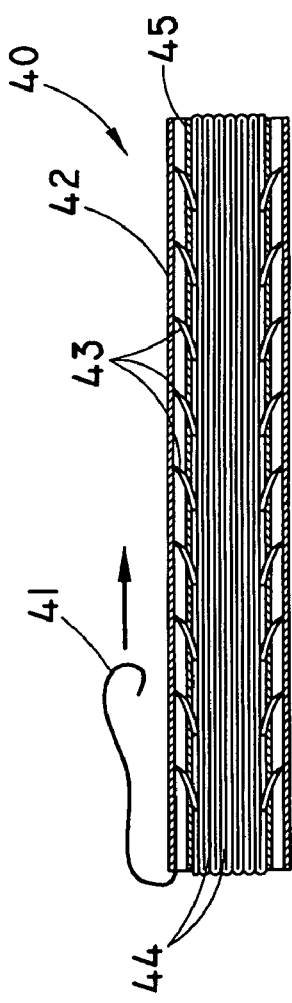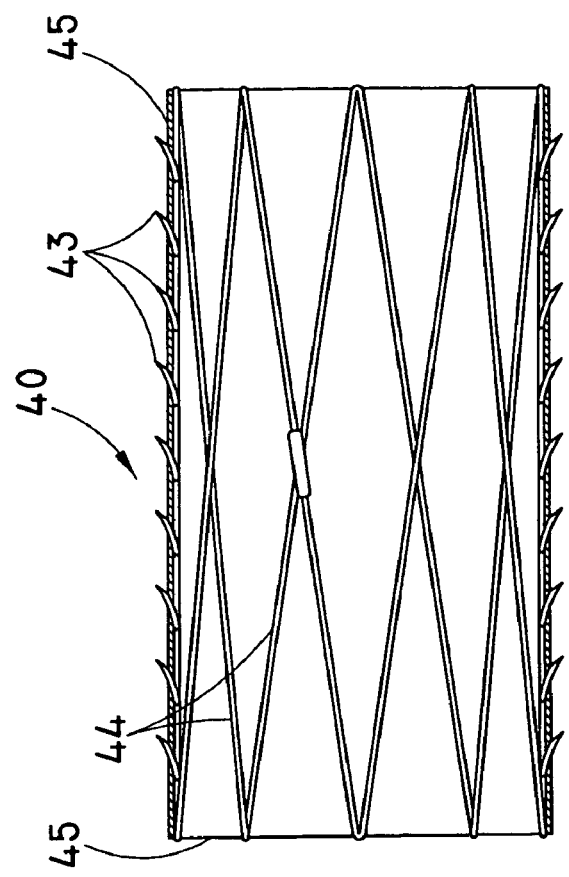
FIG. 6
FIG. 7

STENT/GRAFT DEVICE AND METHOD FOR OPEN SURGICAL PLACEMENT

RELATED APPLICATION

The present patent document claims the benefit of the filing date under 35 U.S.C. §119(e) of Provisional U.S. Patent Application Ser. No. 60/702,924, filed Jul. 27, 2005, which is hereby incorporated by reference.

BACKGROUND

1. Technical Field

The present invention relates generally to the field of stents and stent grafts, and more particularly, to a stent/graft device and method for open surgical, or "intraoperative", placement in a body vessel of a patient.

2. Background Information

Emergency physicians frequently encounter patients having traumatic injury to a body vessel. Significant damage to a body vessel, such as a blood vessel, may expose a patient to deleterious conditions such as the loss of a limb, loss of function of a limb, increased risk of stroke, impairment of neurological functions, and compartment syndrome, among others. Particularly severe cases of vascular injury and blood loss may result in death. Examples of treatments that are commonly performed by emergency physicians to treat vessel injury secondary to trauma include clamping the vessel with a hemostat, use of a balloon tamponade, ligation of the damaged vessel at or near the site of injury, or the insertion of one or more temporary shunts.

In the case of traumatic injury to blood vessels, the use of temporary shunts has been linked to the formation of clots. Shunts are generally placed as a temporary measure to restore blood flow, and to stop excessive blood loss. This may require returning the patient to the operating room for treatment and removal of the clots, often within about 36 to 48 hours of the original repair. When the patient has stabilized (generally a few days later), the shunt is typically removed and replaced with a vascular graft, such as a fabric graft that is sewn into place. Ligation of the damaged vessel may result in muscle necrosis, loss of muscle function, edema, or compartment syndrome with potential limb loss or death.

Due to the nature of the vascular injury that may be encountered, the use of shunts, repairing and/or ligating of a vessel often requires that such treatments be performed at great speed, and with a high degree of physician skill. Such treatments may occupy an undue amount of the time and attention of an emergency physician at a time when other pressing issues regarding the patient's treatment may also require immediate attention. In addition, since the level of particularized skill required may exceed that possessed by the typical emergency physician, particularly traumatic episodes may require the skills of a specially trained physician. Such physicians are specially trained to address the particular trauma, such as a vascular trauma, and to stabilize the patient in the best manner possible under the circumstances of the case.

It would be desirable to provide a system and method for dealing with vascular trauma (arterial and venous) in a manner that is time effective, that addresses the trauma at hand to the extent possible, and that utilizes techniques that may be readily practiced by an emergency physician.

BRIEF SUMMARY

The present invention addresses the problems of the prior art by providing a stent/graft device and method for intraoperative placement in a body vessel.

In one form thereof, the invention comprises a method for intraoperative repair of a damaged portion of a body vessel. A stent/graft device has a length at least as long as a length of the damaged vessel portion undergoing intraoperative repair. The stent/graft device is positioned within the vessel in a manner such that the device spans at least the length of the damaged portion of the vessel. The stent/graft device is engaged with the vessel at the vessel damaged portion in a manner such that migration of the stent/graft device in said vessel is inhibited.

In another form thereof, the invention comprises a stent/graft device for intraoperative repair of a damaged portion of a body vessel. The device comprises an elongated generally cylindrical stent body and a graft material covering at least a portion of the stent body. The device is expandable from a compressed condition having a diameter less than a diameter of the vessel to an expanded condition having a diameter at least as large as the diameter of the vessel. The device is positionable within the vessel in the compressed condition and engageable with the vessel in the expanded condition.

In yet another form thereof, the invention comprises a stent/graft device for intraoperative repair of a damaged portion of a body vessel. The device comprises a generally cylindrical body having a passageway therethrough. A connector is positioned at least one axial end of the body. An axial end of the connector extends into the passageway and another axial end of the connector extends from said body. The axial end extending into the passageway has a diameter such that the end is snugly received in the body. The axial end extending from the body includes a mechanism for effecting engagement with the vessel.

BRIEF DESCRIPTION OF THE DRAWINGS

FIG. 1 is a side view of a stent/graft device for intraoperative placement according to one embodiment of the present invention;

FIG. 2 is a sectional view of the main body of the stent/graft device along lines 2-2 of FIG. 1;

FIG. 3 is a side view of a connector of the stent/graft device of FIG. 1;

FIG. 4 is a side view of fragment of a damaged body vessel that has previously been subjected to a traumatic episode;

FIG. 5 is a side view of the damaged vessel of FIG. 4 with the stent/graft device of FIG. 1 positioned at the site of the vessel trauma;

FIG. 6 is a side view of an alternative embodiment of an expandable stent/graft device suitable for intraoperative placement according to the present invention, with the stent/graft device shown in a compressed condition;

FIG. 7 shows the stent/graft device of FIG. 6 in an expanded condition;

DETAILED DESCRIPTION OF THE DRAWINGS AND THE PRESENTLY PREFERRED EMBODIMENTS

Figure 9:
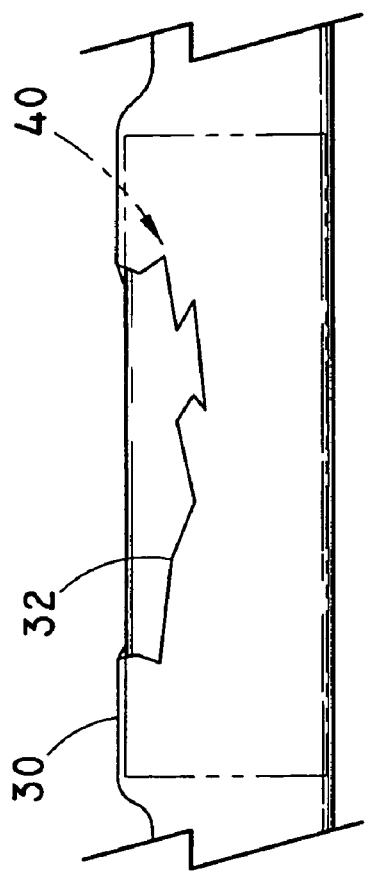
FIG. 9 shows the stent/graft device of FIG. 8 in the damaged vessel in the expanded condition.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 illustrates one embodiment of an inventive stent/graft device 10 for open surgical, or intraoperative, placement. In this embodiment, stent/graft device 10 comprises a generally cylindrical body 12, having a connector 14 disposed at either or both axial ends of cylindrical body 12. Stent/graft device 10 has a size and shape suitable for placement within a body vessel, such as a blood vessel (either an artery or vein), and most particularly, for placement at the site of a vascular trauma.

For convenience, the inventive device is referred to herein as a "stent/graft" device. The device has features in combination with a conventional stent, as well as with a conventional stent graft. In some embodiments of the present invention, one or more conventional expandable stents comprise a part of the actual stent/graft device, and in particular, function as retention members to seal the ends of a tubular graft material to the vessel. In one form, the inventive device comprises a stent graft that is used for intraoperative repair of injury and other trauma to a body vessel, such as a blood vessel.

Typically, stent/graft body 12 comprises a hollow, elongated, generally flexible material, such as a flexible polymeric material, having a lumen 13 extending therethrough. Stent/graft body 12 can be formed from conventional materials well-known in the medical arts, such as silicone, polyurethane, polyamide (nylon), as well as other flexible biocompatible materials. In addition, body 12 can be formed from known fabric graft materials such as woven polyester (e.g. DACRON®) and expanded polytetrafluoroethylene (ePTFE; e.g. GORE-TEX®), or from a bioremodelable material. A bioremodelable material can provide an extracellular matrix that permits, and may even promote, cellular invasion and ingrowth into the material upon implantation. Non-limiting examples of suitable bioremodelable materials include reconstituted or naturally-derived collagenous materials. Suitable collagenous materials may include an extracellular matrix material (ECM) that possesses biotropic properties, such as submucosa, renal capsule membrane, dermal collagen, dura mater, pericardium, fascia lata, serosa, peritoneum or basement membrane layers. Suitable submucosa materials may include, for example, intestinal submucosa, including small intestinal submucosa, stomach submucosa, urinary bladder submucosa, and uterine submucosa.

Connector 14 may comprise any shape suitable for use in fixedly engaging stent/graft device 10 within a body vessel. In the non-limiting example shown in FIG. 3, connector 14 comprises an elongated tubular structure having a main body portion 15, a recessed portion 16 adjacent each axial end of main body portion 15, and a generally frusto-conical end portion 17 at each axial end of the connector. Preferably, connector 14 is sized such that one end of the connector is snugly received within the lumen of stent/graft body 12 up to about the axial midpoint of main connector body portion 15, as shown in FIG. 1. For best results, the outer diameter of main body portion 15 should be at least as large as the inner diameter of flexible cylindrical body 12 to insure a tight and secure fit of connector 14 within the lumen of cylindrical body 12.

Generally, connector 14 will comprise a relatively rigid structure, such as a metal, metal alloy, or a high-strength polymer, having a lumen therethrough. Connector 14 has sufficient strength to maintain its structural integrity upon tying of one or more sutures around the circumference of the connector, in a manner to be described. Generally, any biocompatible composition having the requisite strength may be utilized, as long as the composition has sufficient strength so as to not be unduly compressed upon application of pressure on its outer surface caused by the sutures.

Preferably, one or more sutures 18 are tied around the circumference of stent/graft body 12 to firmly secure connector 14 within stent/graft body lumen 13. For best results, respective sutures 18 are tied at or about the recessed portion 16 of connector 14 that has previously been disposed within lumen 13. In this manner, as the suture is tied about flexible stent/graft body 12, a portion of body 12 is compressed within the recessed portion 16.

Although FIG. 3 illustrates one preferred shape of a connector 14 for use in stent/graft device 10, the connector need not necessarily have the shape shown therein. As one non-limiting alternative, connector 14 may be provided with a simple cylindrical configuration throughout its length. It is most preferable that the connector 14 has a diameter such that it may be snugly received within the axial end portion of stent/graft body 12, and that it is receivable within the lumen of the body vessel undergoing repair. However, as stated, it is believed that recesses 16 are beneficial in providing a recess, or groove, within which sutures 18, 20 can be received as they are tightened around the outer surface of the respective stent/graft body 12 (suture 18), or vessel 30 (suture 20) (FIG. 5), thereby establishing a more secure connection. The optional frusto-conical axial ends 17 of connector 14 facilitate the insertion of the device into the vessel, and improve the ability of stent/graft device 10 to remain anchored within the vessel.

One example of the intraoperative use of stent/graft device 10 in treating a vascular trauma will now be described. FIG. 4 illustrates a blood vessel 30 that has previously been subjected to a traumatic episode. In this case, it will be observed that a portion 32 of blood vessel 30 has been torn away or otherwise severely damaged. As illustrated in FIG. 5, after the body has been opened, stent/graft device 10 is manually placed within vessel 30 by the physician, in a manner such that stent/graft body 12 spans at least the length of damaged vessel portion 32.

In the embodiment shown, stent/graft device 10 is anchored to inhibit migration within vessel 30 by tying one or more sutures 20 around the vessel at an exposed portion of connector 14. For best results, sutures 20 are tied around connector 14 at exposed recess portion 16. In this manner, sutures 20 compress a portion of vessel 30, such that the vessel is pressed within the recess 16 at each axial end to ensure a tight and secure connection, as shown in FIG. 5. Open surgical placement of the inventive stent/graft device in the manner described can generally be accomplished in a minimal amount of time, often on the order of about 2 minutes. To the contrary, conventional repair techniques may take as long as 45 minutes, or even longer in some instances.

A stent/graft device for use in open surgical, or intraoperative, placement according to the present invention need not necessarily be configured as shown in FIG. 1. Other configurations are also suitable for such placement and are considered within the scope of the invention. One alternative embodiment of a stent/graft device 40 suitable for such placement is shown in FIG. 6. In this embodiment, stent/graft device 40 is selectively expandable from a collapsed, or "non-expanded", condition as shown in FIG. 6, to an expanded condition, as shown in FIG. 7.

Stent/graft device 40 comprises an elongated, generally cylindrical stent body 44. Body 44 may be formed, e.g., of one or more wires in a conventional stent crossing pattern of wires. A fabric graft 45 is provided to cover stent body 44 in well-known fashion. The wires forming stent body 44 may be any conventional wires commonly utilized for such purposes, such as metals and metal alloys. Non-limiting examples of suitable compositions include stainless steel and shape memory materials, such as nitinol, as well as compositions that are visible under common medical imaging techniques such as magnetic resonance imaging (MRI). One non-limiting example of a preferred composition that is visible under imaging techniques is titanium. Fabric graft 45 may comprise any graft material well-known in the medical arts, including, but not limited to, the materials described above with reference to stent/graft device 10. The graft material must be capable of expansion as shown in the figures. EPTFE is a particularly preferred graft material. Those skilled in the art will appreciate that other known types of stents and graft materials may be substituted for those shown and described herein.

In FIG. 6, non-expanded stent/graft device 40 is shown positioned within a conventional delivery sheath 42. Sheath 42 is a tubular structure having a conventional mechanism for facilitating the removal of the stent/graft device from the sheath following proper placement within the vessel, such as a pull-tab mechanism or a pusher. In the embodiment of FIG. 6, the removal mechanism comprises a pull-tab type mechanism, namely string 41. When string 41 is pulled in the direction of the arrow, sheath 42 is split in a longitudinal direction, and may thereafter be peeled away from the stent graft. One example of a suitable splittable mechanism is the pull-tab mechanism used in connection with PEEL-AWAY® sheaths, available from Cook Incorporated, of Bloomington, Ind. Alternatively, other conventional mechanisms for removing a device from a delivery sheath, and/or for splitting a sheath for removal, may be utilized. Sheaths of the type shown and described herein are well known in the art, and those skilled in the art will appreciate that many known sheaths may be substituted for the sheath shown and described herein, each of which is considered within the scope of the invention.

As stated, stent/graft device 40 is expandable from a compressed condition to an expanded condition. Thus, following delivery of the stent/graft by splitting the sheath or other appropriate delivery mechanism, stent/graft device 40 expands from the contracted condition shown in FIG. 6 to the expanded condition shown in FIG. 7. Preferably, stent/graft device 40 is provided with anchoring structure, such as barbs 43, provided along at least a portion of the outer circumference of the device to anchor the expanded stent/graft device in the vessel. Those skilled in the art will appreciate that many appropriate anchoring structures are known in the art, such as hooks, "fish-scales", and the like, any of which may be utilized in place of, or in addition to, the barbs shown in FIGS. 6 and 7. Although the embodiment of FIGS. 6 and 7 includes barbs along the entire length of the stent/graft, this is not required, and barbs can alternatively be positioned at one or more discrete locations along the length of the stent/graft device. Similarly, although the barbs shown in the figures each have a sharp tip pointing in the same direction, this is exemplary only, and barb tips can be provided that face in the same, or opposite, directions. Those skilled in the art can readily select an appropriate arrangement of barb tips for a particular use.

Figure 8:
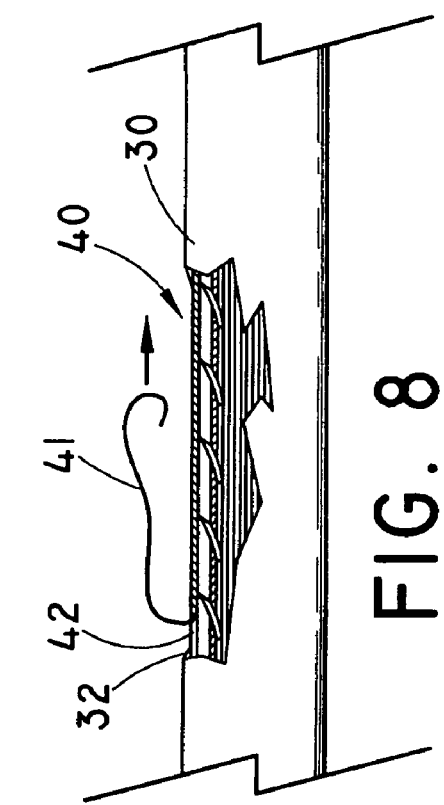
FIG. 8 illustrates the stent/graft device of FIG. 6 as positioned in a damaged vessel, with the stent/graft device in the compressed condition.

FIGS. 8 and 9 illustrate the intraoperative placement of stent/graft device 40 at the site of a vascular trauma, such as the trauma illustrated in FIG. 4. As shown in FIG. 8, sheath 42, having stent/graft device 40 loaded therein in a collapsed state, is intraoperatively placed within vessel 30 at the site of vascular trauma 32. Sheath 42 is split by pulling string 41 in the direction of the arrow, and the sides of sheath 42 may be peeled or otherwise removed in conventional fashion from the stent/graft device. Once stent/graft device 40 is freed from the constraints of sheath 42, it thereafter expands in the vessel, as shown in FIG. 9. Preferably, stent/graft device 40 has an expanded outer diameter at least as large, and preferably somewhat larger, than the inner diameter of vessel 30.

Figure 10:
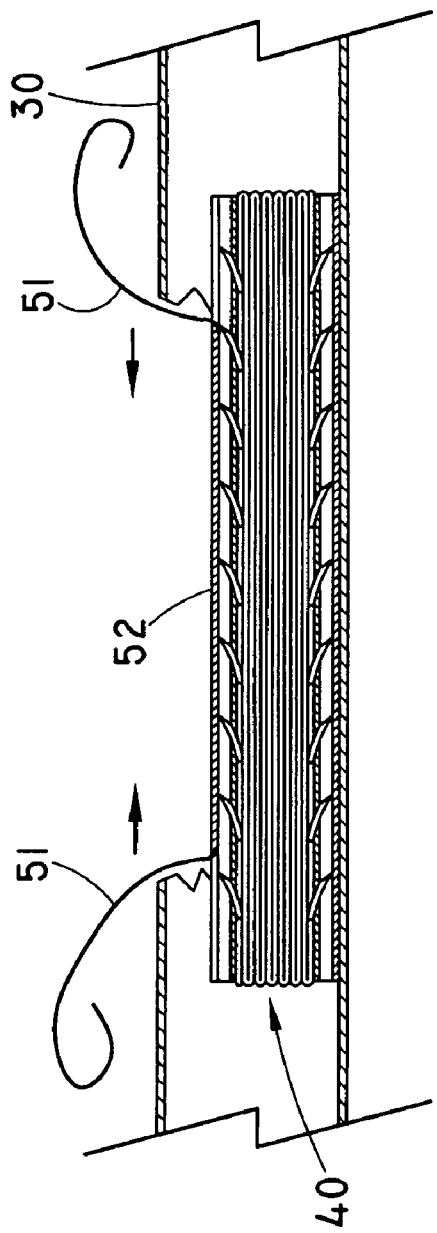
FIG. 10 is a side view of an alternative embodiment of a stent/graft device positioned in a compressed condition in a damaged vessel.

FIG. 10 illustrates a modification of the arrangement shown in FIGS. 6-9. In this case, delivery sheath 52 is provided with two pull strings, rather than the single string shown in FIG. 6. In this variation, each of the strings 51 is positioned at a separate axial end of the sheath 52. The strings are then pulled in the direction of the respective arrows to split the sheath. The sheath is then pulled away, freeing the stent/graft device 40 for expansion within the vessel 30.

Figure 11:
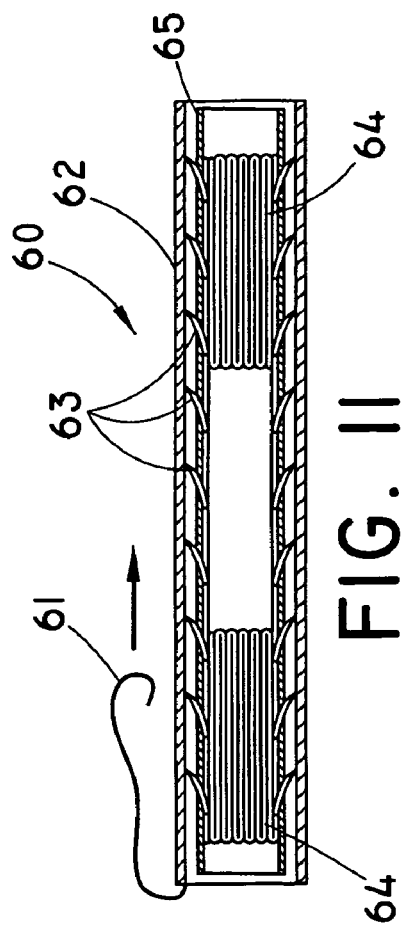
FIG. 11 is a side view of another alternative embodiment of an expandable stent/graft device according to the present invention, with the stent/graft shown in a compressed condition.
Figure 12:
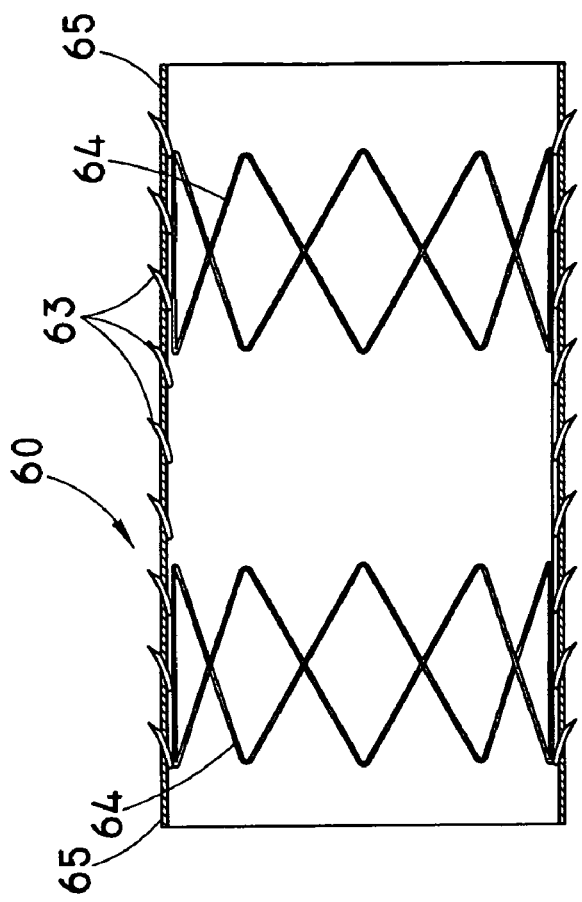
FIG. 12 shows the stent/graft device of FIG. 11 in an expanded condition.

Another embodiment of the present invention is illustrated in FIGS. 11 and 12. In this embodiment, stent/graft device 60 comprises an arrangement of multiple axially-aligned stents 64, rather than the single wire stent body 44 as illustrated in FIGS. 6 and 7. In the embodiment shown, there are two stents 64 disposed at opposite ends of expandable stent/graft device 60. A sheath 62 having one or more pull strings 61 is provided as before. Stent graft body 65 can be formed of any of the compositions previously described, and if desired, may include a plurality of barbs 63 or similar anchoring structures.

Although the arrangement shown in FIGS. 11 and 12 includes two stents 64 disposed at axial ends of device 60, numerous alternative arrangements are within the scope of the invention. As one possible alternative, the device can include a series of stents disposed along all, or a part of, the length of the stent/graft device. Such stents can be connected to each other, be placed immediately adjacent to each other, or spaced a discrete distance from each other. The fabric of the stent/graft device need not necessarily cover, or span, all stented portions of the device, although sufficient fabric should be provided to at least span the site of the vascular damage. Thus, with this embodiment, a stent/graft device can be provided having a plurality of stents disposed along the length of the device. If desired, the stent/graft device can be sized such that it has a greater length and/or a greater number of stents than would typically be required for use. The physician can then trim the stent/graft device to a desired length. In this manner, the medical facility need not maintain a large number of stent/graft devices of different lengths, but rather, can stock one or more elongated devices that can be trimmed by the physician to the desired length immediately prior to use.

With an embodiment including multiple expandable stents, such as the embodiment illustrated in FIGS. 11 and 12, the splittable outer sheath need not necessarily extend the entire length of the device. Rather, a separate splittable sheath may be provided to cover each of the stented portions of the stent/graft, and the unstented portions may remain uncovered. In this manner, each of the sheaths can be split with, e.g. a string or a conventional mechanism, to effect controlled expansion of the stents, and concomitantly, of the graft material, within the damaged vessel.

According to the present invention, a stent/graft device can have a length of virtually any size for use in treating a vascular trauma. Preferably, a stent/graft device will have a length between about 1 and 10 cm, more preferably, between about 3 and 8 cm, and still more preferably, about 6 or 7 cm. It is preferred that the stent/graft will be slightly longer than the length of the damaged vascular portion undergoing repair. For convenience, the stent/graft can be structured such that at least a portion of either, or both, axial ends of the stent graft can be trimmed by the physician to a desired length.

The stent/graft device described herein can also include a coating of one or more therapeutic agents. Therapeutic agents for use as bio-compatible coatings are well known in the art. Non-limiting examples of suitable bio-active agents that may be applied to the stent/graft device include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bio-active agents may be applied for a particular use. The bio-active agent can be incorporated into, or otherwise applied to, portions of the stent/graft device by any suitable method that permits adequate retention of the agent material and the effectiveness thereof for its intended purpose.

Although the device has been described in connection with its primary intended use for repair of vascular trauma, those skilled in the art will appreciate that the device may also be used to repair other traumatic conditions. Non-limiting examples of such conditions include aneurysms, such as abdominal aorta aneurysms.

It is therefore intended that the foregoing detailed description be regarded as illustrative rather than limiting, and that it be understood that it is the following claims, including all equivalents, that are intended to define the spirit and scope of this invention.

The invention claimed is:

1. A method for open surgical repair of a damaged portion of a body vessel of a patient that has been subjected to a traumatic episode, comprising:
    surgically opening an open air pathway from an outer layer of skin to said damaged vessel portion;
    positioning a stent/graft device at said surgical opening for insertion through said open air pathway, said stent/graft device having a length at least as long as a length of said damaged vessel portion undergoing repair, said stent/graft device comprising an elongated generally cylindrical stent and a graft material covering at least a portion of said stent, said device being expandable from a compressed condition having a diameter less than a diameter of the vessel to an expanded condition having a diameter at least as large as the diameter of the vessel, said stent/graft device being loaded into a sheath capable of maintaining said stent/graft device in said compressed condition;
    inserting said sheath having said stent/graft device loaded therein in said compressed condition into said damaged vessel portion through said open air pathway, such that said device at least spans said damaged vessel portion length; and
    removing said sheath from said stent/graft device at said site such that said stent/graft device expands to said expanded condition and engages said vessel, in a manner such that migration of said stent/graft device in said vessel is inhibited.

2. The method of claim 1, wherein said stent/graft device includes an anchoring mechanism for anchoring said device to said vessel and thereby inhibiting said migration.

3. The method of claim 2, wherein said anchoring mechanism comprises barbs provided along at least a portion of an outer circumference of the stent/graft device.

4. The method of claim 3, wherein said sheath includes a mechanism for selectively splitting said sheath for effecting expansion of said device.

5. The method of claim 1, wherein said sheath includes a mechanism for selectively splitting said sheath for effecting expansion of said device.

6. The method of claim 5, wherein said mechanism comprises a pull-tab.

7. The method of claim 6, wherein the pull-tab comprises a string aligned for splitting said sheath upon pulling said string in a first direction.

8. The method of claim 1, wherein said stent/graft device includes a coating comprising at least one therapeutic agent.

9. A method for open surgical repair of a damaged portion of a body vessel, comprising:
    surgically opening an open air pathway from an outer layer of skin to said damaged vessel portion;
    positioning an assembly comprising a sheath and a stent/graft device at said surgical opening for insertion through said open air pathway, said stent/graft device received in said sheath in a compressed condition having a diameter less than a diameter of the vessel, and expandable therefrom to an expanded condition having a diameter at least as large as the diameter of the vessel, said stent/graft device having a length at least as long as the length of said damaged vessel portion undergoing repair, said stent/graft device comprising a plurality of axially spaced stents, and a graft material spanning axially adjacent stents and covering at least a portion of said axially adjacent stents, said assembly including a mechanism for selectively splitting said sheath for effecting expansion of said stents to the expanded condition;
    inserting said sheath into said damaged vessel portion through said open air pathway when said stents are in said compressed condition, such that the stent/graft device at least spans said damaged vessel portion; and
    splitting said sheath, thereby effecting expansion of said stents to said expanded condition such that said stent/graft device engages said vessel.

10. The method of claim 9, wherein said stent/graft device includes an anchoring mechanism for anchoring said device to said vessel when said device is in the expanded condition.

11. The method of claim 10, wherein said anchoring mechanism comprises barbs provided along at least a portion of an outer circumference of the stent/graft device.

12. The method of claim 9, wherein said plurality of axially spaced stents comprises a pair of stents, said stents spaced such that one of said stents is positioned at each axial end of said stent/graft device.

13. The method of claim 12, wherein a respective sheath is provided for each of said stents, each sheath enclosing a separate one of said stents when said stent is in a compressed condition, each said sheath being selectively removable for effecting expansion of said stent.

14. The method of claim 9, wherein said mechanism for selectively splitting said sheath comprises a pull-tab.

15. The method of claim 14, wherein said pull-tab comprises a string aligned for splitting said sheath upon pulling said string in a first direction.

16. The method of claim 9, wherein the mechanism for selectively splitting the sheath comprises a pair of pull-strings, a first one of said pull-strings being aligned along said sheath to be pulled in a first direction, and a second one of said pull-strings being aligned along said sheath to be pulled in a second direction, opposite from said first direction, whereupon said splitting step comprises pulling each of said pull-strings in said respective direction.

17. A method for open surgical repair of a fragmented portion of a body vessel that has been subjected to a traumatic episode, comprising:

surgically opening an open air pathway from an outer layer of skin to said fragmented vessel portion;

positioning a stent/graft device at said surgical opening for repair, the stent/graft device having a length at least as long as the length of the fragmented vessel portion undergoing repair, the stent/graft device comprising a pair of axially spaced stents, and a graft material spanning the stents, the stents being expandable from a compressed condition having a diameter less than a diameter of the vessel to an expanded condition having a diameter at least as large as the diameter of the vessel, the stent/graft device being loaded into a sheath mechanism, the sheath mechanism including one or more sheath members aligned for maintaining the stents in the compressed condition;

inserting the sheath mechanism having the stent/graft device loaded therein into the fragmented vessel portion through said open air pathway, and aligning the sheath mechanism along the vessel such that the stent/graft device at least spans the fragmented vessel portion; and removing the sheath mechanism, thereby effecting expansion of the stents to the expanded condition such that the stent/graft device engages the vessel.

18. The method of claim 17, wherein the stent/graft device includes an anchoring mechanism for anchoring the device to the vessel when the device is in the expanded condition.

19. The method of claim 18, wherein the anchoring mechanism comprises at least one anchor member at each axial end thereof.

20. The method of claim 17, wherein the sheath mechanism includes one or more pull-tabs for splitting the sheath for removal thereof.

21. The method of claim 17, wherein said sheath mechanism comprises two sheath members, each of said sheath members includes a pull-string for splitting said sheath member, and wherein said removing step is carried out by pulling each of said pull strings to split the respective sheath members.

22. The method of claim 17, wherein the fragmented portion of the body vessel comprises a portion that has been removed from a remainder of the body vessel, and the inserting step comprises manually placing the sheath mechanism having the stent/graft device loaded therein at a site of the removed vessel portion.

* * * * *